United States Patent [19]

Mitchell et al.

[11] Patent Number: 5,981,689
[45] Date of Patent: Nov. 9, 1999

[54] POLY(VINYLAMINE)-BASED SUPERABSORBENT GELS AND METHOD OF MANUFACTURING THE SAME

[75] Inventors: Michael A. Mitchell, Lake Zurich; Thomas W. Beihoffer, Arlington Heights; Leticia L. Trzupek, Hoffman Estates; Jerald W. Darlington, Jr., Marengo, all of Ill.

[73] Assignee: Amcol International Corporation, Arlington Heights, Ill.

[21] Appl. No.: 08/974,119

[22] Filed: Nov. 19, 1997

[51] Int. Cl.$^6$ .................. C08F 8/00; C08F 8/12; C08G 69/00
[52] U.S. Cl. .......... 528/229; 528/220; 528/310; 525/327.4; 525/328.2; 525/328.3; 525/329.3; 525/329.4; 525/329.7; 525/428
[58] Field of Search .................... 528/310, 229, 528/220; 525/327.4, 328.2, 328.3, 329.3, 329.4, 329.7, 428

[56] References Cited

U.S. PATENT DOCUMENTS

| | | |
|---|---|---|
| 4,018,826 | 4/1977 | Gless, Jr. et al. ............... 260/583 P |
| 4,798,871 | 1/1989 | Lai et al. ............... 525/328.2 |
| 4,804,793 | 2/1989 | Lai et al. ............... 574/445 |
| 4,818,598 | 4/1989 | Wong ............... 428/284 |
| 4,843,118 | 6/1989 | Lai et al. ............... 524/555 |
| 5,085,787 | 2/1992 | Pinschmidt, Jr. et al. ............ 252/8.551 |
| 5,274,018 | 12/1993 | Tanaka et al. ............ 524/166 |
| 5,491,199 | 2/1996 | Ford et al. ............... 525/362 |
| 5,669,894 | 9/1997 | Goldman et al. ............... 604/368 |

FOREIGN PATENT DOCUMENTS

| | | | |
|---|---|---|---|
| WO 96/15162 | 5/1996 | WIPO | ............ C08F 20/06 |
| WO 96/15163 | 5/1996 | WIPO | ............ C08F 20/56 |
| WO 96/15180 | 5/1996 | WIPO | ............ C08J 5/02 |
| WO 96/17682 | 6/1996 | WIPO | ............ B01J 20/00 |
| WO 98/24832 | 6/1998 | WIPO | ............ C08J 3/075 |
| WO 98/37149 | 8/1998 | WIPO | ............ C08L 101/14 |

*Primary Examiner*—P. Hampton-Hightower
*Attorney, Agent, or Firm*—Marshall, O'Toole, Gerstein, Murray & Borun

[57] ABSTRACT

Poly(vinylamine)-based superabsorbent gels are disclosed. The superabsorbent gels either comprise a mixture of a poly(vinylamine) polymer and an acidic water-absorbing polymer, like polyacrylic acid, or comprise a salt of a poly(vinylamine) polymer. An improved method of preparing poly(vinylamine) also is disclosed.

27 Claims, No Drawings

POLY(VINYLAMINE)-BASED SUPERABSORBENT GELS AND METHOD OF MANUFACTURING THE SAME

FIELD OF THE INVENTION

The present invention relates to superabsorbent gels containing a poly(vinylamine), or a salt thereof, and to an improved method of manufacturing a poly(vinylamine). The superabsorbent gels comprise a poly(vinylamine), and preferably a poly(vinylamine) admixed with an acidic superabsorbent polymer, like a polyacrylic acid, or comprise a salt of a poly(vinylamine).

BACKGROUND OF THE INVENTION

Water-absorbing resins are widely used in sanitary goods, hygienic goods, wiping cloths, water-retaining agents, dehydrating agents, sludge coagulants, disposable towels and bath mats, disposable door mats, thickening agents, disposable litter mats for pets, condensation-preventing agents, and release control agents for various chemicals. Water-absorbing resins are available in a variety of chemical forms, including substituted and unsubstituted natural and synthetic polymers, such as hydrolysis products of starch acrylonitrile graft polymers, carboxymethylcellulose, crosslinked polyacrylates, sulfonated polystyrenes, hydrolyzed polyacrylamides, polyvinyl alcohols, polyethylene oxides, polyvinylpyrrolidines, and polyacrylonitriles.

Such water-absorbing resins are termed "superabsorbent polymers," or SAPs, and typically are lightly crosslinked hydrophilic polymers. SAPs are generally discussed in Goldman et al. U.S. Pat. No. 5,669,894. SAPs can differ in their chemical identity, but all SAPs are capable of absorbing and retaining amounts of aqueous fluids equivalent to many times their own weight, even under moderate pressure. For example, SAPs can absorb one hundred times their own weight, or more, of distilled water. The ability to absorb aqueous fluids under a confining pressure is an important requirement for an SAP used in a hygienic article, like a diaper.

The dramatic swelling and absorbent properties of SAPs are attributed to (a) electrostatic repulsion between the charges along the polymer chains, and (b) osmotic pressure of the counter ions. It is known, however, that these absorption properties are drastically reduced in solutions containing electrolytes, such as saline, urine, and blood. The polymers do not function as effective SAPs in the presence of such physiologic fluids.

The decreased absorbency of electrolyte-containing liquids is illustrated by the absorption properties of a typical, commercially available SAP, i.e., sodium polyacrylate, in deionized water and in 0.9% by weight sodium chloride (NaCl) solution. The sodium polyacrylate can absorb 146.2 grams (g) of deionized water per gram of SAP (g/g) at 0 psi, 103.8 g of deionized water per gram of polymer at 0.28 psi, and 34.3 g of deionized water per gram of polymer of 0.7 psi. In contrast, the same sodium polyacrylate is capable of absorbing only 43.5 g, 29.7 g, and 24.8 g of 0.9% aqueous NaCl at 0 psi, 0.28 psi, and 0.7 psi, respectively. The absorption capacity of SAPs for body fluids, like urine or menses, therefore, is dramatically lower than for deionized water because such fluids contain electrolytes. This dramatic decrease in absorption is termed "salt poisoning."

The salt poisoning effect has been explained as follows. Water-absorption and water-retention characteristics of SAPs are attributed to the presence of ionizable functional groups in the polymer structure. The ionizable groups typically are carboxyl groups, a high proportion of which are in the salt form when the polymer is dry, and which undergo dissociation and salvation upon contact with water. In the dissociated state, the polymer chain contains a plurality of functional groups having the same electric charge and, thus, repel one another. This electronic repulsion leads to expansion of the polymer structure, which, in turn, permits further absorption of water molecules. Polymer expansion, however, is limited by the crosslinks in the polymer structure, which are present in a sufficient number to prevent solubilization of the polymer.

It is theorized that the presence of a significant concentration of electrolytes interferes with dissociation of the ionizable functional groups, and leads to the "salt poisoning" effect. Dissolved ions, such as sodium and chloride ions, therefore, have two effects on SAP gels. The ions screen the polymer charges and the ions eliminate the osmotic imbalance due to the presence of counter ions inside and outside of the gel. The dissolved ions, therefore, effectively convert an ionic gel into a nonionic gel, and swelling properties are lost.

The most commonly used SAP for absorbing electrolyte-containing liquids, like urine, is neutralized polyacrylic acid, i.e., containing at least 50%, and up to 100%, neutralized carboxyl groups. Neutralized polyacrylic acid, however, is susceptible to salt poisoning. Therefore, to provide an SAP that is less susceptible to salt poisoning, either an SAP different from neutralized polyacrylic acid must be developed, or the neutralized polyacrylic acid must be modified or treated to at least partially overcome the salt poisoning effect.

Prior investigators have attempted to counteract the salt poisoning effect and thereby improve the performance of SAPs with respect to absorbing electrolyte-containing liquids, such as menses and urine. For example, Tanaka et al. U.S. Pat. No. 5,274,018 discloses an SAP composition comprising a swellable hydrophilic polymer, like polyacrylic acid, and an amount of an ionizable surfactant sufficient to form at least a monolayer of surfactant on the polymer. In another embodiment, a cationic gel, like a gel containing quaternized ammonium groups and in the hydroxide (i.e., OH) form, is used with an anionic gel (i.e., a polyacrylic acid) to remove electrolytes from the solution by ion exchange.

Wong U.S. Pat. No. 4,818,598 discloses admixing a fibrous anion exchange material, like DEAE cellulose, and a hydrogel, like a polyacrylate, to improve absorption properties. WO 96/17681 discloses admixing an anionic SAP, like polyacrylic acid, with a polysaccharide-based cationic SAP to overcome the salt poisoning effect. Similarly, WO 96/15163 discloses admixing a cationic SAP having at least 20% of the functional groups in a basic (i.e., OH) form with a cationic exchanges resin, i.e., a nonswelling ion exchange resin, having at least 50% of the functional groups in the acid form. WO 96/15180 discloses an absorbent material comprising an anionic SAP, e.g., a polyacrylic acid and an anion exchange resin, i.e., a nonswelling ion exchange resin.

These references disclose combinations that attempt to overcome the salt poisoning effect. It would be desirable, however, to provide an SAP that exhibits exceptional absorbency and retention, like a sodium polyacrylate, and, therefore, can be used alone as an SAP. It also would be desirable to admix such an SAP with polyacrylic acid, or another acid-containing SAP, to overcome the salt poisoning effect.

SUMMARY OF THE INVENTION

The present invention is directed to poly(vinylamine)-based superabsorbent gels. A poly(vinylamine) polymer can be used in conjunction with an acidic water-absorbing resin, like polyacrylic acid, to help overcome the salt poisoning effect, or a salt of a poly(vinylamine) polymer can be used alone as an SAP. The poly(vinylamine) polymer also can be used, alone, as an SAP to absorb and retain acidic media. More particularly, the poly(vinylamine) used as an SAP, or as a component of an SAP, is lightly crosslinked and, in preferred embodiments, is surface treated to improve absorption properties.

Accordingly, one aspect of the present invention is to provide an improved method of manufacturing a poly (vinylamine) comprising vinylamine monomer units, and which can be crosslinked using a suitable polyfunctional vinyl monomer. The present method substantially reduces the amount of residual N-vinylamide monomer in the poly (N-vinylamide) precursor of the poly(vinylamine), and, therefore, eliminates the stringent purification procedures, or reduces the long polymerization reaction times, previously used to overcome the problem of residual monomer content. Consequently, the present improved process reduces process time and production costs.

Another aspect of the present invention is to provide an SAP having absorbency and retention properties comparable to a conventional SAP, like sodium polyacrylate. A present SAP is produced by neutralizing a poly(vinylamine) with a sufficient amount of acid, like hydrochloric acid, such that at least about 10%, i.e., about 10% to 100%, of the amine-functional groups are neutralized. The resulting poly (vinylamine) salt is an excellent SAP for absorbing aqueous media.

In accordance with another important aspect of the present invention, a lightly crosslinked poly(vinylamine), alone and unneutralized, can be used to absorb and retain acidic aqueous media. The acidic aqueous media converts the low-absorbing poly(vinylamine) to a highly absorbing poly(vinylamine) salt, i.e., converts the polymer to an SAP, during absorption. A poly(vinylamine), therefore, is an excellent resin for cleaning acid spills and the remediation of acidic species.

Yet another aspect of the present invention is to provide an improved SAP that overcomes the salt poisoning effect of electrolytes. In particular, the improved SAP material contains a mixture of an acidic swellable resin, like polyacrylic acid, and a poly(vinylamine).

These and other aspects and advantages of the present invention will become apparent from the following detailed description of the preferred embodiments.

DETAILED DESCRIPTION OF THE PREFERRED EMBODIMENTS

The present invention is directed to: (a) an improved method of manufacturing poly(vinylamine), (b) poly (vinylamine) and poly(vinylamine) salts and their use as SAPs, and (c) an improved SAP material comprising an admixture of a poly(vinylamine) and an acidic water-absorbing resin.

(a) An Improved Method of Manufacturing Poly (vinylamine)

Poly(vinylamine), and salts derived therefrom, are known polymers. For example, the following patents disclose the synthesis or manufacture of poly(vinylamine): U.S. Pat. No. 4,798,871; U.S. Pat. No. 4,843,118; and U.S. Pat. No. 4,804,793. In addition, U.S. Pat. No. 4,018,826 discloses a process for preparing poly(vinylamine) and salts thereof. Ford et al. U.S. Pat. No. 5,491,199 discloses the preparation of formate-free poly(vinylamine) by heating the polymer in the presence of transition metal catalyst.

The above patents generally disclose polymers of N-vinylformamide that subsequently are hydrolyzed. Upon hydrolysis, the poly(N-vinylformamide) is converted into a poly(vinylamine). Hydrolysis can be performed under acid or basic conditions. The cationic charge on the resulting vinylamine, i.e., the charge density, is related to the pH of the medium. At a low pH, the poly(vinylamine) is protonated and has a high cationic charge density. Conversely, at a high pH, the poly(vinylamine) is not protonated, and the polymer has a substantially reduced cationic charge density, if any.

In general, an uncrosslinked poly(vinylamine) is a water-soluble polymer that has many practical applications, such as in water treatment, personal care products, and ion exchange resins. Poly(vinylamine) is rendered water insoluble by crosslinking the polymer. Although polyvinylamines, and salts thereof, are well known, it has not heretofore been suggested that such polymers can be used as an SAP.

Typically, a poly(vinylamine) polymer is produced by hydrolysis of poly(N-vinylformamide), under either acid or basic conditions. Poly(vinylamine) also can be produced from other poly(N-vinylamides), like poly(N-vinylacetamide), poly(N-vinylpropionamide), and poly(N-vinylsuccinamide). It is desirable that hydrolysis of the poly(vinylamide) is substantially to essentially complete, i.e., about 10% to 100% complete, and preferably about 30% to 100% complete. To achieve the full advantage of the present invention, at least about 50%, and more preferably at least about 90%, of the amide groups are hydrolyzed to an amine functionality. The aminefunctional polymer can contain other copolymerizable units, i.e., other monoethylenically unsaturated monomers, as long as the polymer is substantially, i.e., at least 10%, and preferably at least 25%, vinylamine units. To achieve the full advantage of the present invention, the polymer contains at least 50%, and more preferably at least 75%, vinylamine units.

If residual monomer or other impurities are present in the poly(vinylamide), hydrolysis conditions can lead to crosslinking, which increases the molecular weight of the poly(vinylamine) and can result in undesirable and unpredictable gel formation. Therefore, current methods of synthesizing poly(vinylamine) require either a rigorous purification of the poly(N-vinylformamide), or an extremely long reaction time and a relatively high reaction temperature to ensure that all the residual poly(N-vinylformamide) monomer is consumed during the polymerization.

The production of poly(vinylamine) would be facilitated, and production costs decreased, by an improved method of removing residual N-vinylamide monomers from the poly (N-vinylamide). Therefore, in accordance with an important feature of the present invention, an improved method of manufacturing poly(vinylamine) is disclosed.

As set forth above, polymerization of N-vinylformamide, followed by hydrolysis, is the most common method of producing poly(vinylamine). The polymerization can be performed in the presence or absence of a crosslinker, i.e., a polyfunctional organic compound. However, residual N-vinylformamide monomer, or other monomer impurities, like aldehydes, can cause crosslinking and undesired gel formation during hydrolysis. In accordance with an important feature of the present invention, it has been found that the problem of residual monomer content, and the presence of other impurities, can be overcome by the use of suitable scavenging agents to remove the residual monomer and other impurities from the poly(N-vinylamide). The use of scavenging agents has the advantage of greatly reducing the process time, and costs, currently invested to insure that all the N-vinylamide monomer and other impurities are consumed prior to hydrolysis.

In accordance with an important feature of the present invention, a scavenging agent is added to a poly(N-vinylamide), prior to hydrolysis, in an amount of about 0.1% to about 3%, and preferably about 0.1% to about 2%, by weight, based on the weight of N-vinylamide monomer used in the polymerization. To achieve the full advantage of the present invention, the scavenging agent is added in an amount of about 0.1% to about 1%, by weight, based on the weight of N-vinylamide monomer.

The scavenging agent can be any compound capable of reacting with N-vinylamides, like N-vinylformamide, and other aldehydic impurities, like formaldehyde or acetaldehyde, under hydrolysis conditions, i.e., a temperature of about 25° C. to about 80° C. for about 4 to about 24 hours in the presence of an acid or a base. Typically, a scavenging agent is capable of reacting with an aldehyde in about 1 minute to about 10 minutes at a temperature of about 20° C. to about 80° C.

Examples of scavenging agents include, but are not limited to: (a) oxidizing agents, like potassium permanganate, ammonia silver salts (Tollen's Reagent), potassium dichromate, and hydrogen peroxide; (b) reducing agents, like catalytic hydrogenation, lithium aluminum hydride, sodium borohydride, diborane, aluminum hydride, LiAlH (O.t-Bu)$_3$ (lithium aluminum tri-t-butoxy hydride), LiAlH (OCH$_3$)$_3$ (lithium aluminum trimethoxy hydride), zinc (mercury) and concentrated hydrochloric acid, and hydrazine and a base; (c) Grignard reagents, like aryl and alkyl magnesium halides; (d) sodium or potassium cyanide with sodium bisulfite; (e) sodium bisulfite; and (f) ammonia derivatives, like hydroxylamine, hydrazine, substituted hydrazines, e.g., phenyl hydrazine, and semicarbazine. A reducing agent is a preferred scavenging agent, and sodium borohydride is a most preferred scavenging agent. Such scavenging agents have the advantages of being inexpensive, greatly reducing the reaction time to form a poly(N-vinylamide), and eliminating the need to purify the poly(N-vinylamide).

To achieve the full advantage of the present invention, the scavenging agent is an aqueous solution containing sodium borohydride, e.g., about 10% to about 15% by weight, and sodium hydroxide. The sodium borohydride acts quickly, is highly effective, and is inexpensive. As an added advantage, the sodium hydroxide is useful in a subsequent basic hydrolysis of the poly(N-vinylamide). Prior to hydrolyzing the poly(N-vinylamide), the poly(N-vinylamide) and scavenging agent are held at about 25° C. to about 80° C. for about 1 minute to about 10 minutes to eliminate essentially all, i.e., about 95% to 100%, of the residual monomers and impurities.

After using a scavenging agent to remove residual monomers and other impurities, the poly(N-vinylamide) is hydrolyzed. The amount of acid or base used to hydrolyze the poly(N-vinylamide) in solution can vary widely, and is generally added in a molar ratio of acid or base to N-vinylamide monomer content of the initially formed polymer of about 0.05:1 to about 3:1, preferably about 0.3:1 to about 1:1. To achieve the full advantage of the present invention, the molar ratio of acid or base to N-vinylamide monomer is about 0.7:1 to about 1:1.

Generally, hydrolysis is achieved with a suitable acid, such as an inorganic acid, for example, hydrochloric acid, hydrobromic acid, hydrofluoric acid, sulfuric acid, nitric acid, phosphoric acid, and the like. In addition, suitable bases, such as an inorganic base, for example, sodium hydroxide, ammonia, ammonium hydroxide, potassium hydroxide, and the like, can also be used. Hydrolysis is conducted at a temperature of about 25° C. to about 100° C. for about 4 to about 24 hours.

The degree of hydrolysis is controlled by the amount of acid or base, the reaction temperature, and/or the reaction time. In general, greater amounts of acid or base, higher reaction temperatures, and longer reaction times result in higher degrees of hydrolysis.

The present method, therefore, is an improved method of manufacturing either crosslinked or uncrosslinked poly (vinylamine). The following examples illustrate the improved method in the manufacture of uncrosslinked poly (vinylamine).

EXAMPLE 1

N-vinylformamide (400 g, 5.6 mole) was dissolved in 3,000 g of deionized water, then the resulting monomer solution was sparged with argon for one hour. In a separate vessel, 5 g of 2,2'-azobis(2-amidinopropane) hydrochloride initiator (i.e., V-50 initiator available from Wako Pure Chemical Industries, Inc., Osaka, Japan) was dissolved in 70 g of deionized water, then the resulting initiator solution was sparged with argon for one-half hour. A 7 g portion of the initiator solution was added to the monomer solution, and the remainder of the initiator solution was added to the monomer solution over an hour period while heating the resulting reaction mixture to about 45° C. The reaction temperature was maintained at about 45° C. for about 4 hours. The reaction mixture then was heated to 55° C. and held for two hours. Finally, 20 g of a 15% by weight aqueous V-50 solution was added to the reaction mixture, and the polymerization reaction was held at 65° C. for 12 hours to provide poly(N-vinylformamide).

The aqueous poly(N-vinylformamide) solution then was heated to about 70° C., while 20 g of a 12% by weight sodium borohydride solution (in 41% aqueous sodium hydroxide) was added to the polymer solution. After the scavenger solution was added, 480 g of 50% aqueous sodium hydroxide was added to the polymer solution, and the resulting solution was stirred for about 8 hours at about 70° C. to hydrolyze the poly(N-vinylformamide).

If desired, the resulting poly(vinylamine) solution then can be purified by ultrafiltration. In this optional purification, the poly(vinylamine) solution was diluted with 3 liters of deionized water. The diluted solution then was ultrafiltered with a 100,000 molecular weight cut-off tangential flow ultrafiltration module. The diluted polymer solution was washed with 25 liters of deionized water, and then concentrated to 2,500 ml to give a 4 wt % solution of sodium formate-free poly(vinylamine).

Example 1 was repeated, but the scavenger step using sodium borohydride was omitted. During hydrolysis, the aqueous solution of poly(N-vinylformamide) gelled. Gelling was attributed to impurities present in the N-vinylformamide monomer that were not removed in a scavenging step.

The following example illustrates the ability of a scavenger, like sodium borohydride, to reduce the reaction time in the synthesis of a poly(vinylamine).

EXAMPLE 2

A five liter flask was charged with 400 g of N-vinylformamide monomer and 2,970 g of deionized water, and the resulting monomer solution was sparged with argon for one hour. Separately, an initiator solution was prepared by dissolving 5 g of V-50 in 67 g of deionized water, and sparging with argon for 0.5 hours. A portion of the initiator solution (7 g) was added to the monomer solution. The remainder of the initiator solution was added to the monomer solution over a one-hour time period, while the resulting reaction mixture was heated to 45° C. The reaction mixture was held at 45° C. for 2.5 hours, then heated to 55° C. and held for an additional 2.5 hours, and finally heated to 65° C. and held for an additional one hour. Next, 20 g of 12% sodium borohydride in a 41% aqueous sodium hydroxide solution was added to the reaction mixture, followed immediately by 480 g of a 50% aqueous sodium hydroxide solution. The reaction mixture quickly turned pink in color but then returned to colorless. The hydrolysis step was continued at 70° C. for an additional 8 hours. The resulting poly(vinylamine) solution can then be purified, if desired, by ultrafiltration as set forth in Example 1. In the absence of a sodium borohydride scavenger, the reaction requires an additional several hours to react all the N-vinylformamide monomers and other impurities, as set forth in Example 1.

EXAMPLE 3

Freshly distilled N-vinylformamide (250 g, 3.5 mole) and 2.8 g of 15% V-50 initiator were dissolved in 400 g of deionized water, then the resulting reaction solution was sparged with argon for 15 minutes. Next, the reaction solution was poured into a glass pan and cured at 15 mW/cm² of UV light for 25 minutes. The polymerization was exothermic, eventually reaching about 100° C. The resulting concentrated poly(N-vinylformamide) solution was very viscous.

The concentrated poly(N-vinylformamide) solution (312 g) then was diluted with 2 liters of deionized water, and the diluted polymer solution was heated to 70° C. Six (6) g of a sodium borohydride solution (15% by weight of 41% aqueous sodium hydroxide) was added dropwise to the heated polymer solution over a five-minute time period, followed by the addition of 143 g of 50% aqueous sodium hydroxide. The resulting solution was maintained at 70° C. for 8 hours to hydrolyze the poly(N-vinylformamide), then cooled and purified as in Example 1.

The present improved method of manufacturing poly(vinylamine) also can be used in processes wherein poly(vinylamine) is derived from, for example, poly(N-vinylacetamide), poly(N-vinylpropionamide), poly(N-vinylsuccinamide), and similar N-vinylcarboxamides.

The present improved method of manufacturing a poly(vinylamine) can also be used in the manufacture of a crosslinked poly(vinylamine). As described above, SAPs are crosslinked to a sufficient extent such that the polymer is water insoluble. Crosslinking serves to render the poly(vinylamine) polymers substantially water insoluble, and, in part, serves to determine the absorptive capacity of the polymers. For use in absorption applications, the poly(vinylamine) is lightly crosslinked, i.e., has a crosslinking density of less than about 20%, and preferably less than about 10%, and most preferably about 0.01% to about 7%.

When used, a crosslinking agent most preferably is included in an amount of less than about 7 wt %, and typically about 0.1 wt % to about 5 wt %, based on the total weight of monomers. A poly(vinyl-amine) can be crosslinked by two different pathways. One pathway utilizes olefinically unsaturated crosslinking monomers that copolymerize with the N-vinylamide, and, therefore, form a part of the polymeric backbone. The crosslinked poly(N-vinylamide) then is hydrolyzed to provide crosslinked polyvinylamine.

Examples of crosslinking polyvinyl monomers include, but are not limited to, polyacrylic (or polymethacrylic) acid esters represented by the following formula (I); and bisacrylamides, represented by the following formula (II).

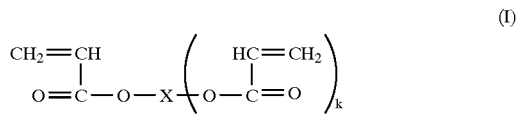

wherein x is ethylene, propylene, trimethylene, hexamethylene, 2-hydroxypropylene, $—(CH_2CH_2O)_nCH_2CH_2—$, or

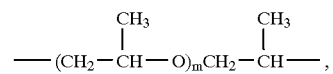

n and m are each an integer 5 to 40, and k is 1 or 2;

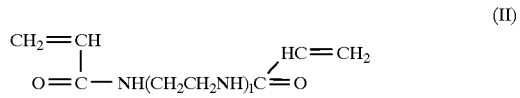

wherein l is 2 or 3.

The compounds of formula (I) are prepared by reacting polyols, such as ethylene glycol, propylene glycol, trimethylolpropane, 1,6-hexanediol, glycerin, pentaerythritol, polyethylene glycol, or polypropylene glycol, with acrylic acid or methacrylic acid. The compounds of formula (II) are obtained by reacting polyalkylene polyamines, such as diethylenetriamine and triethylenetetramine, with acrylic acid.

Specific crosslinking monomers include, but are not limited to, 1,4-butanediol diacrylate, 1,4-butanediol dimethacrylate, 1,3-butylene glycol diacrylate, 1,3-butylene glycol dimethacrylate, diethylene glycol diacrylate, diethylene glycol dimethacrylate, ethoxylated bisphenol A diacrylate, ethoxylated bisphenol A dimethacrylate, ethylene glycol dimethacrylate, 1,6-hexanediol diacrylate, 1,6-hexanediol dimethacrylate, neopentyl glycol dimethacrylate, polyethylene glycol diacrylate, polyethylene glycol dimethacrylate, triethylene glycol diacrylate, triethylene glycol dimethacrylate, tripropylene glycol diacrylate, tetraethylene glycol diacrylate, tetraethylene glycol dimethacrylate, dipentaerythritol pentaacrylate, pentaerythritol tetraacrylate, pentaerythritol triacrylate, trimethylolpropane triacrylate, trimethylolpropane trimethacrylate, tris(2-hydroxyethyl) isocyanurate triacrylate, tris(2-hydroxyethyl)isocyanurate trimethacrylate, divinyl esters of a polycarboxylic acid, diallyl esters of a polycarboxylic acid, triallyl terephthalate, diallyl maleate, diallyl fumarate, hexamethylenebismaleimide, trivinyl trimellitate, divinyl adipate, diallyl succinate, a divinyl ether of ethylene glycol, cyclopentadiene diacrylate, or mixtures thereof. Compounds like divinylbenzene and divinyl ether also can be used to crosslink the poly(N-vinylamide). Especially preferred crosslinking agents are N,N'-methylenebisacrylamide, N,N'-methylenebismethacrylamide, ethylene glycol dimethacrylate, and trimethylolpropane triacrylate.

The following example illustrates a crosslinked poly(vinylamine) prepared in accordance with the present invention.

EXAMPLE 4

A monomer mixture containing N-vinylformamide (250 grams), deionized water (250 grams), methylenebisacrylamide (1.09 grams), and V-50 initiator (0.42 grams) was placed in a shallow dish, then polymerized under an ultraviolet lamp as set forth in Example 3 until the mixture polymerized into a rubbery gel. The concentrated poly(N-vinylformamide) then was treated with a sodium borohydride/sodium hydroxide solution, as set forth in Example 1, to yield a lightly crosslinked poly(vinylamine). Sodium formate present in the crosslinked poly(vinylamine) can be removed by washing the resin with acetone/water mixtures, or by other suitable methods known to persons skilled in the art.

Poly(vinylamine) also can be crosslinked in solution by suspending or dissolving uncrosslinked poly(vinylamine) in an aqueous medium, then adding a di- or poly-functional compound capable of crosslinking the poly(vinylamine) by reaction with the amino groups of the polymer. Such crosslinking agents include, for example, multifunctional aldehydes (e.g., glutaraldehyde), multifunctional acrylates (e.g., butanediol diacrylate, TMPTA), halohydrins (e.g., epichlorohydrin), dihalides (e.g., dibromopropane), disulfonate esters (e.g., $WS(O_2)O-(CH_2)_n-OS(O)_2W$, wherein n is one to 10, and W is methyl or tosyl), multifunctional epoxies (e.g., ethylene glycol diglycidyl ether), multifunctional esters (e.g., dimethyl adipate), multifunctional acid halides (e.g., oxalyl chloride), multifunctional carboxylic acids (e.g., succinic acid), carboxylic acid anhydrides (e.g., succinic anhydride), organic titanates (e.g., TYZOR AA from DuPont), melamine resins (e.g., CYMEL 301, CYMEL 303, CYMEL 370, and CYMEL 373 from Cytec Industries, Wayne, N.J.), hydroxymethyl ureas (e.g., N,N'-dihydroxymethyl-4,5-dihydroxyethyleneurea), and multifunctional isocyanates (e.g., toluene diisocyanate). Crosslinking agents also are disclosed in Pinschmidt, Jr. et al. U.S. Pat. No. 5,085,787, incorporated herein by reference, and in EP 450 923.

In general, the crosslinking agent should be water soluble and possess sufficient reactivity with poly(vinylamine) such that crosslinking occurs in a controlled fashion, preferably at a temperature of about 25° C. to about 150° C. A preferred crosslinking agent is ethylene glycol diglycidyl ether (EGDGE), a water-soluble diglycidyl ether.

The following example illustrates light crosslinking of a sodium formate-free poly(vinylamine) of the present invention using a polyfunctional crosslinking agent that reacts with the amino groups of the polymer.

EXAMPLE 5

To 2 liters of a 3% by weight aqueous poly(vinylamine) solution was added 0.18 g of ethyleneglycol diglycidyl ether (EGDGE). The resulting mixture was stirred to dissolve the EGDGE, then the mixture was heated to about 60° C. and held for one hour to gel. The gel was heated to about 80° C. and held until about 90% of the water was removed. The resulting gel then was extruded and dried to a constant weight at 80° C. The dried, lightly crosslinked poly(vinylamine) then was cryogenically milled to form a granular material capable of absorbing water or acid solutions. The gel exhibited the following absorption characteristics in 0.1 M hydrochloric acid (HCl):

AUNL[1]=59.3 g/g
AUL[2] (0.28 psi)=37.8 g/g
AUL[2] (0.7 psi)=26.4 g/g

[1] Absorption under no load; and
[2] Absorption under load.

Absorption under load (AUL) is a measure of the ability of an SAP to absorb fluid under an applied pressure. The AUL was determined by the following method, as disclosed in U.S. Pat. No. 5,149,335, incorporated herein by reference.

An SAP (0.160 g+/−0.001 g) is carefully scattered onto a 140-micron, water-permeable mesh attached to the base of a hollow plexiglass cylinder with an internal diameter of 25 mm. The sample is covered with a 100 g cover plate and the cylinder assembly weighed. This gives an applied pressure of 20 $g/cm^2$ (0.28 psi). Alternatively, the sample can be covered with a 250 g cover plate to give an applied pressure of 51 $g/cm^2$ (0.7 psi). The screened base of the cylinder is placed in a 100 mm petri dish containing 25 milliliters of a test solution (usually 0.9% saline), and the polymer is allowed to absorb for 1 hour (or 3 hours). By reweighing the cylinder assembly, the AUL (at a given pressure) is calculated by dividing the weight of liquid absorbed by the dry weight of polymer before liquid contact. As discussed hereafter, the poly(vinylamine) particles also can be surface treated with a crosslinking agent, like ethyleneglycol diglycidyl ether, to give an absorbent having improved performance under external pressure.

In a preferred embodiment, a lightly crosslinked poly(vinylamine) is subjected to a process step wherein the surface of the poly(N-vinylamine) is further crosslinked. It has been found that surface crosslinking of a poly(vinylamine) enhances the ability of the polymer to absorb and retain aqueous media under load.

Surface crosslinking is achieved by spraying poly(vinylamine) particles with an isopropyl alcohol solution of a surface crosslinking agent to wet predominantly only the outer surfaces of the poly(vinylamine) particles. Surface crosslinking and drying of the polymer then is performed, preferably by heating at least the wetted surfaces of the poly(vinylamine) particles.

Typically, the poly(vinylamine) particles are surface treated with an alcoholic solution of a surface crosslinking agent. The particles can be in the form of granules, a foam, beads, flakes, fibers, or powders, for example. The solution contains about 0.01% to about 4%, by weight, surface crosslinking agent, and preferably about 0.4% to about 2%, by weight, surface crosslinking agent in a suitable solvent. The solution can be applied as a fine spray onto the surface of freely tumbling poly(vinylamine) particles at a ratio of about 1:0.01 to about 1:0.5 parts by weight poly(vinylamine) to solution of surface crosslinking agent. The surface crosslinker is present in an amount of 0% to about 1%, by weight of the poly(vinylamine), and preferably 0% to about 0.5% by weight. To achieve the full advantage of the present invention, the surface crosslinker is present in an amount of about 0.001% to about 0.1% by weight.

The crosslinking reaction and drying of the surface-treated poly(vinylamine) particles are achieved by heating the surface-treated polymer at a suitable temperature, e.g., about 25° C. to about 150° C., and preferably about 105° C. to about 120° C. However, any other method of reacting the crosslinking agent to achieve surface crosslinking of the poly(vinylamine) particle, and any other method of drying the poly(vinylamine) particles, such as microwave energy, or the like, can be used.

Suitable surface crosslinking agents include the di- or poly-functional molecules capable of reacting with amino groups and crosslinking poly(vinylamine). Preferably, the surface crosslinking agent is alcohol or water soluble and possesses sufficient reactivity with a poly(vinylamine) such that crosslinking occurs in a controlled fashion at a temperature of about 25° C. to about 150° C.

Nonlimiting examples of suitable surface crosslinking agents include:

(a) dihalides and disulfonate esters, for example, compounds of the formula

Z—(CH$_2$)$_p$—Z, wherein p is a number from 2 to 12, and Z, independently, is halo (preferably bromo), tosylate, mesylate, or other alkyl or aryl sulfonate esters;

(b) multifunctional aziridines;

(c) multifunctional aldehydes, for example, glutaraldehyde, trioxane, paraformaldehyde, terephthaldehyde, malonaldehyde, and glyoxal, and acetals and bisulfites thereof;

(d) halohydrins, like epichlorohydrin;

(e) multifunctional epoxy compounds, for example, ethylene glycol diglycidyl ether, bisphenol A diglycidyl ether, and bisphenol F diglycidyl ether, (f) multifunctional carboxylic acids and esters, acid chlorides, and anhydrides derived therefrom, for example, di- and poly-carboxylic acids containing two to twelve carbon atoms, and the methyl and ethyl esters, acid chlorides, and anhydrides derived therefrom, like oxalic acid, adipic acid, succinic acid, dodecanoic acid, malonic acid, and glutaric acid, and esters, anhydrides, and acid chlorides derived therefrom;

(g) organic titanates, like TYZOR AA, available from E.I. DuPont de Nemours, Wilmington, Del.;

(h) melamine resins, like the CYMEL resins available from Cytec Industries, Wayne, N.J.;

(i) hydroxymethyl ureas, like N,N'-dihydroxymethyl-4,5-dihydroxyethylene urea; and (j) multifunctional isocyanates, like toluene diisocyanate, isophorone diisocyanate, xylene diisocyanate, and hexamethylene diisocyanate.

A preferred surface crosslinking agent is ethylene glycol diglycidyl ether (EGDGE), which is a water-soluble diglycidyl ether which crosslinks poly(vinylamine) at a temperature of about 25° C. to about 150° C.

The following Example 6 illustrates surface treatment and crosslinking of a lightly crosslinked poly(vinylamine).

EXAMPLE 6

Divinylbenzene crosslinker (1.085 g, 55% active, by weight, in styrene/ethylstyrene), aqueous V-50 initiator (2.541 g, 15%), and N-vinylformamide (245 g, 3.45 moles) were mixed in 350 g of deionized water. The resulting solution was sparged with argon for 15 minutes, and then polymerized under UV light (15 mW/cm$^2$) for one hour. The resulting gel was extruded, dried at 100° C., and milled to produce particles of lightly crosslinked poly(vinylamine).

A portion of the poly(N-vinylformamide) particles (82 g) was hydrolyzed by dispersing the particles in a solution containing 168 g cyclohexane, 112 g 1-butanol, and 46 g of powdered sodium hydroxide. The resulting suspension then was heated at about 70° C. for about 6 hours. Next, 150 g of deionized water was added to the suspension, and the organic solvents were decanted. Acetone (230 g) then was added to collapse the gel and remove the sodium formate by-product. The water/acetone wash was repeated three more times, and the gel was dried then remilled. The resulting poly(vinylamine) gel then was surface treated with ethylene glycol diglycidyl ether at various levels, and dried at 145° C. to provide a surface crosslink.

The poly(vinylamine) then was tested for an ability to absorb and retain 0.1 M hydrochloric acid.

TABLE 1

| Surface Crosslink Level (ppm)[3] | AUNL[1] and AUL[2] (0.1M HCl) | | |
|---|---|---|---|
| | No Load | 0.28 psi | 0.7 psi |
| 0 | 51 | 23 | 9.9 |
| 100 | 47 | 27 | 19 |
| 500 | 47 | 27 | 19 |
| 1000 | 46 | 28 | 20 |
| 2000 | 41 | 26 | 20 |

[3]ppm—parts per million of surface crosslinker.

The absorption data shows that surface crosslinking substantially improves the absorption under load of a poly(vinylamine), especially at a load of 0.7 psi.

(b) Poly(vinylamine)-based SAPs

Poly(vinylamine) typically does not function as an SAP in its neutral form because there is no ionic charge on the polymer. The driving force for water absorption and retention therefore is lacking. However, when converted to a salt, or used in conjunction with an acidic water-absorbing resin, like a polyacrylic acid, a poly(vinylamine) then behaves likes an SAP. It should be understood that a poly(vinylamine) produced either by the above-described improved method, or by a prior, conventional method, can be used in a poly(vinylamine)-based SAP.

(i) Salts of Poly(vinylamine)

As previously discussed, sodium poly(acrylate) is considered the best SAP, and, therefore, is the most widely used SAP in commercial applications. Sodium poly(acrylate) has polyelectrolytic properties that are responsible for its superior performance in absorbent applications. These properties include a high charge density, and charge relatively close to the polymer backbone.

Poly(vinylamine) is a neutral polymer, and, accordingly, does not possess the polyelectrolytic properties necessary to provide an SAP. However, poly(vinylamine) salts have polyelectrolytic properties sufficient to provide an SAP. The poly(vinylamine) used to provide an SAP is a lightly crosslinked poly(vinylamine), and preferably is surface crosslinked, as set forth above.

Such lightly crosslinked, and optionally surface crosslinked, poly(vinylamine) polymers are converted into salts by methods known in the art. For example, the preparation of poly(vinylamine HCl) by the addition of hydrochloric acid to a poly(vinylamine) is set forth in Pinschmidt, Jr. et al. U.S. Pat. No. 5,085,787, and in Gless, Jr. et al. U.S. Pat. No. 4,018,826, or by hydrolysis of a poly(N-vinylamide) with hydrochloric acid.

A poly(vinylamine) salt useful as an SAP, however, is not limited to the hydrochloride salt. Poly(vinylamine) can be reacted with a variety of acids to provide a poly(vinylamine) salt useful as an SAP, but the preferred acids are mineral acids. To achieve the full advantage of the present invention, the poly(vinylamine) salt is a hydrochloride salt.

To demonstrate the ability of a poly(vinylamine) salt to act as an SAP, the lightly crosslinked poly(vinylamine) of Example 5 was converted to the hydrochloride salt by methods well known in the art. The poly(vinylamine) salt was tested for its ability to absorb and retain deionized water and electrolyte-containing aqueous media (i.e., 0.9% by weight aqueous sodium chloride).

In particular, poly(vinylamine) samples, as prepared in Example 5, were converted to the hydrochloride salt using different amounts of 1N hydrochloric acid (HCl). The resulting gels of poly(vinylamine) salt then were dried and evaluated for an ability to absorb a 0.9% by weight aqueous NaCl solution. The results are summarized in Table 2.

TABLE 2

| Mole % HCL[4] | AUNL[1] | AUL[2] (0.28 psi) | AUL[2] (0.7 psi) |
|---|---|---|---|
| 0 | 18.7 | 13.7 | 12.6 |
| 30 | 31.6 | 21.5 | 15.9 |
| 50 | 39.8 | 25.6 | 20.1 |
| 70 | 43.0 | 23.4 | 13.5 |
| 100 | 28.5 | 9.1 | 9.5 |

[4]mole % HCl added to the poly(vinylamine) based on the moles of N-vinylformamide monomer used to prepare the poly(vinylamine).

The absorbency results summarized in Table 2 show that absorbency increases dramatically, both under load and under no load, when the poly(vinylamine) is converted to a hydrochloride salt, especially in the range of about 30 to about 70 mole % conversion to the salt. In accordance with an important feature of the present invention, a poly (vinylamine) exhibits the properties of an SAP when converted to a salt in an amount of about 10 to about 100, and preferably about 20 to about 90, mole percent. To achieve the full advantage of the present invention, the poly (vinylamine) is converted to a salt in an amount of about 25 to about 75 mole %, based on the weight of N-vinylamide monomer used to prepare the poly(vinylamine).

In another test, a lightly crosslinked poly(vinylamine), as prepared in Example 6, was surface treated with various levels of ethylene glycol diglycidyl ether (EGDGE) in isopropyl alcohol, followed by drying and curing at 80° C. The surface crosslinked granules of lightly crosslinked polyvinylamine then were partially neutralized (i.e., 50 mole %) with 1N HCl. The surface crosslinked polyvinylamine salt, then was tested for an ability to absorb and retain a 0.9% aqueous NaCl solution. The results are summarized in Table 3, and show that a neutralized and surface crosslinked poly(vinylamine) shows an improvement in AUL.

TABLE 3

| Surface Crosslink Level of EGDGE (ppm)[4] | AUNL[1] | AUL[2] (0.28 psi) | AUL[2] (0.7 psi) |
|---|---|---|---|
| 0 | 35.8 | 16.6 | 9.3 |
| 100 | 35.3 | 18.9 | 11.3 |
| 500 | 31.5 | 16.3 | 11.2 |
| 1000 | 31.3 | 17.8 | 11.5 |
| 2000 | 28.8 | 18.0 | 11.9 |

(ii) Poly(vinylamine) in SAPs

As illustrated above, poly(vinylamine), in its free base form, does not function as an SAP for neutral-to-basic aqueous media. Similarly, polyacrylic acid, in its free acid form, does not function as an SAP for neutral-to-acidic aqueous media. In each case, the polymer has a low charge density, and, accordingly, a major driving force for absorption and retention, i.e., electrostatic repulsion, is missing. In contrast, partially neutralized polyacrylic acid has a sufficient charge density, and is currently used as an SAP by itself. Similarly, as disclosed above, poly(vinylamine) salts have a high charge density and are excellent SAPs.

However, a poly(vinylamine), in its free base form, can act as an absorbent for acidic aqueous media, i.e., media having a pH less than 7, as illustrated in Examples 5 and 6, wherein one gram of poly(vinylamine) absorbed 59.3 g and 51 g of 0.1 M hydrochloric acid under no load, respectively. The acidic media protonates the amino groups of the poly (vinylamine), thereby providing sufficient charge density for the protonated poly(vinylamine) to perform as an SAP. Accordingly, poly(vinylamine), by itself, can be used to absorb acidic aqueous media, for example, to absorb an acid spill.

It also has been found that poly(vinylamine) polymers, in their free base form, are useful components in superabsorbent materials further containing an acidic water-absorbing resin. For example, a superabsorbent material of the present invention is an admixture of a poly(vinylamine) and an acidic water-absorbing resin, like polyacrylic acid. The present superabsorbent materials are particularly useful with respect to absorbing and retaining aqueous media containing electrolytes.

Currently, superabsorbent materials containing two absorbing components, i.e., bi-component SAP materials, are being investigated as an improved class of SAPs. Typically, one component is a water-absorbing resin, and the second component acts in an ion exchange capacity to remove electrolytes from an aqueous media.

In contrast, the present invention is directed to a bi-component SAP material comprising two uncharged, slightly crosslinked polymers, each of which is capable of swelling and absorbing aqueous media. When contacted with water, the two uncharged polymers neutralize each other to form a superabsorbent material. Neither polymer in its uncharged form behaves as an SAP by itself when contacted with water. The present bi-component superabsorbent material, therefore, contains two resins, one acidic and one basic, which are capable of acting as an absorbent material in their polyelectrolyte form. While polyacrylic acid is an excellent choice for the acidic resin, until the present invention, there has not been an adequate basic resin.

Therefore, in accordance with an important feature of the present invention, poly(vinylamine) is used as the basic resin for a bi-component SAP material. The poly (vinylamine) is lightly crosslinked, and the poly (vinylamine) particles preferably are surface crosslinked to improve absorbency characteristics. The poly(vinylamine) and acid resin combination behaves like an SAP in the presence of water, and especially brackish water. The poly (vinylamine) can be prepared by the improved method disclosed herein, or by prior methods known in the art. Crosslinking and surface crosslinking can be performed as set forth above.

The poly(vinylamine) is a basic resin that is admixed with an acidic resin. The acidic resin can be any resin that acts as an SAP in its neutralized form. The acidic resin typically contains a plurality of carboxylic acid, sulfonic acid, phosphonic acid, phosphoric acid, or sulfuric acid moieties, or a mixture thereof.

Examples of acidic resins include, but are not limited to, polyacrylic acid, hydrolyzed starch-acrylonitrile graft copolymers, starch-acrylic acid graft copolymers, saponified vinyl acetate-acrylic ester copolymers, hydrolyzed acrylonitrile copolymers, hydrolyzed acrylamide copolymers, ethylene-maleic anhydride copolymers, isobutylene-maleic anhydride copolymers, poly(vinylsulfonic acid), poly (vinylsulfuric acid), poly(vinylphosphoric acid, sulfonated polystyrene, poly(vinylphosphonic) acid, and mixtures thereof. The preferred acidic resins are the polyacrylic acids.

The poly(vinylamine) is present in its uncharged, i.e., free base, form, and the acidic resin is present in its free acid form. It is envisioned that a low percentage, i.e., 25%. or less, of the amine and acid functionalities can be in their charged form, due to processing, for example. The low percentage of charged functionalities does not adversely affect performance of the superabsorbent material, but the amount of charged functionalities should be minimized.

The poly(vinylamine) and acidic resin are admixed in a weight ratio of about 5:95 to about 95:5, and preferably about 10:90 to about 90:10. To achieve the full advantage of the present invention, the resins are admixed in a weight ratio of about 30:70 to about 70:30. A present bi-component SAP material is prepared by simply admixing particles of the poly(vinylamine) and acidic resin to provide a uniform particulate material.

To illustrate a present bi-component SAP material, the following examples were prepared and tests performed:

EXAMPLE 7

Powdered poly(vinylamine), as prepared in Example 5 (particle size 210–710 µm) was admixed with lightly crosslinked polyacrylic acid (particle size 210–710 µm, 0% neutralized) in a weight ratio of 37% poly(vinylamine) to 63% polyacrylic acid. The absorbency characteristics of the resulting bi-component SAP were tested and compared to the absorbency characteristics with respect to a 0.96 by weight aqueous NaCl solution. The results are set forth in Table 4.

TABLE 4

|  | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
|---|---|---|---|---|---|---|
| Poly(vinylamine)/ Polyacrylic Acid Blend | 21.2 | 18.6 | 28.3 | 23.8 | 20.5 | 36.3 |
| Poly(vinylamine) | 14.2 | 14.4 | 21.4 | 15 | 14.3 | 23.4 |

Table 4 shows that the poly(vinylamine)/polyacrylic acid blend has substantially improved absorption properties compared to poly(vinylamine) alone.

The bi-component SAP materials are especially useful in articles designed to absorb and retain liquids, especially electrolyte-containing liquids. Such articles include, for example, diapers and catamenial devices.

Many modifications and variations of the invention as hereinbefore set forth can be made without departing from the spirit and scope thereof and, therefore, only such limitations should be imposed as are indicated by the appended claims.

What is claimed is:

1. A method of manufacturing a poly(vinylamine) comprising the steps of:
   (a) forming a monomer mixture comprising;
      (i) an N-vinylamide,
      (ii) 0% to 90%, by weight of monomers in the mixture, of one or more monoethylenically unsaturated monomers, and
      (iii) 0% to about 10%, by weight of monomers in the monomer mixture, of a polyvinyl monomer;
   (b) polymerizing monomers of the monomer mixture to form a poly(N-vinylamide) mixture;
   (c) adding about 0.1% to 3.0%, by weight of the N-vinylamide in the monomer mixture, of a scavenging agent to the poly(N-vinylamide) mixture;
   (d) allowing the scavenging agent to react for a sufficient time to remove residual N-vinylamide and impurities from the poly(N-vinylamide) mixture;
   (e) then adding a sufficient amount of an acid or a base to the poly(N-vinylamide) mixture to form a hydrolysis mixture and hydrolyze a poly(N-vinylamide) to the poly(vinylamine).

2. The method of claim 1 wherein the monomer mixture is free of the polyvinyl monomer, and further comprises the steps of;
   (f) isolating the poly(vinylamine) from the hydrolysis mixture;
   (g) adding the poly(vinylamine) to a solvent to form a poly(vinylamine) mixture; and
   (h) adding about 0.1% to about 10%, by weight of poly(vinylamine), of a polyfunctional compound which reacts with amino groups of the poly(vinylamine) to the poly(vinylamine) mixture to form a crosslinked poly(vinylamine).

3. The method of claim 2 further comprising the steps of:
   (i) isolating the crosslinked poly(vinylamine) of step (h) as a solid;
   (j) applying a surface crosslinking agent which reacts with amino groups of the crosslinked poly(vinylamine) to the solid crosslinked poly(vinylamine) in a sufficient amount to wet the surfaces of the solid crosslinked poly(vinylamine); and
   (k) heating the wetted crosslinked poly(vinylamine) for a sufficient time and at a sufficient temperature to dry the solid crosslinked poly(vinylamine) and form surface crosslinks thereon.

4. The method of claim 1 wherein the monomer mixture contains the polyvinyl monomer to provide a crosslinked poly(vinylamine), and further comprises the steps of
   (f) isolating the crosslinked poly(vinylamine) of step (e) as a solid;
   (g) applying a surface crosslinking agent which react with amino groups of the crosslinked poly(vinylamine) to the solid crosslinked poly(vinylamine) in a sufficient amount to wet the surfaces of the solid crosslinked poly(vinylamine); and
   (h) heating the wetted crosslinked poly(vinylamine) for a sufficient time and at a sufficient temperature to dry the solid crosslinked poly(vinylamine) and form surface crosslinks thereon.

5. The method of claim 1 wherein the N-vinylamide is selected from the group consisting of N-vinylformamide, N-vinylacetamide, N-vinylsuccinamide, N-vinylpropionamide, and mixtures thereof.

6. The method of claim 1 wherein the monomer mixture further comprises an azo polymerization initiator.

7. The method of claim 1 wherein about 0.1% to about 20% of the scavenging agent is added to the poly(N-vinylamide) mixture.

8. The method of claim 1 wherein about 0.1% to about 1% of the scavenging agent is added to the poly(N-vinylamide) mixture.

9. The method of claim 1 wherein the scavenging agent reacts with an an aldehyde in about 1 to about 10 minutes at a temperature of about 20° C. to about 80° C.

10. The method of claim 1 wherein the scavenging agent is selected from the group consisting of an oxidizing agent, a reducing agent, a Grignard reagent, a cyanide and a bisulfite, sodium bisulfite, and an ammonia derivative.

11. The method of claim 10 wherein the oxidizing agent is selected from the group consisting of potassium permanganate, ammonia silver salts, potassium dichromate, and hydrogen peroxide.

12. The method of claim 10 wherein the reducing agent is selected from the group consisting of catalytic hydrogenation, lithium aluminum hydride, sodium borohydride, diborane, aluminum hydride, $LiAlH(O.t\text{-}Bu)_3$, $LiAlH(OCH_3)_3$, zinc (mercury) and concentrated hydrochloric acid, and hydrazine and a base.

13. The method of claim 10 wherein the ammonia derivative is selected from the group consisting of hydroxylamine, hydrazine, a substituted hydrazine, phenyl hydrazine, and semicarbazine.

14. The method of claim 1 wherein the scavenger comprises sodium borohydride.

15. The method of claim 1 wherein the scavenger reacts with the poly(N-vinylamide) mixture for about 1 minute to about 10 minutes at a temperature of about 25° C. to about 80° C.

16. The method of claim 1 wherein the poly(N-vinylamide) mixture is hydrolyzed using a mole ratio of acid or base to N-vinylamide of 0.05:1 to about 3:1.

17. The method of claim 1 wherein the poly(N-vinylamide) mixture is hydrolyzed with a base.

18. The method of claim 1 wherein about 10% to 100% of the amide groups of the poly(N-vinylamide) are hydrolyzed.

19. The method of claim 1 wherein the polyvinyl monomer comprises

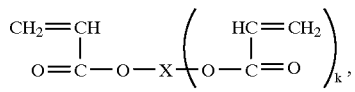

wherein x is ethylene, propylene, trimethylene, hexamethylene, 2-hydroxypropylene, —(CH$_2$CH$_2$O)$_n$CH$_2$CH$_2$—, or

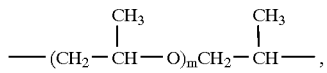

n and m are an integer 5 to 40, and k is 1 or 2;

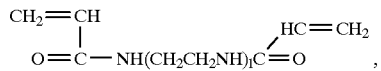

wherein 1 is 2 or 3; or a mixture thereof.

20. The method of claim 1 wherein the polyvinyl monomer comprises divinylbenzene, divinyl ether, or a mixture thereof.

21. The method of claim 2 wherein the polyfunctional compound is selected from the group consisting of a multifunctional aldehyde, a multifunctional acrylate, a halohydrin, a dihalide, a disulfonate ester, a multifunctional epoxy, a multifunctional ester, a multifunctional acid halide, a multifunctional carboxylic acid, a carboxylic acid anhydride, an organic titanate, a melamine resin, a hydroxymethyl urea, a multifunctional isocyanate, and mixtures thereof.

22. The method of claim 3 wherein the surface crosslinking agent is selected from the group consisting of (a) a dihalide or a disulfonate ester having the formula

wherein p is an integer 2 to 12 and Z, independently, is halo, tosylate, mesylate, an alkyl sulfonate ester, or an aryl sulfonate ester;

(b) a multifunctional aziridine;

(c) a multifunctional aldehyde, and acetals and bisulfites thereof;

(d) a halohydrin;

(e) a multifunctional epoxy compound;

(f) a multifunctional carboxylic acid containing two to twelve carbon atoms, and methyl and ethyl esters, acid chlorides, and anhydrides derived therefrom;

(g) an organic titanate;

(h) a melamine resin;

(i) a hydroxymethyl urea; and (j) a multifunctional isocyanate.

23. The method of claim 4 wherein the surface crosslinking agent is selected from the group consisting of (a) a dihalide or a disulfonate ester having the formula

wherein p is an integer 2 to 12 and Z, independently, is halo, tosylate, mesylate, an alkyl sulfonate ester, or an aryl sulfonate ester;

(b) a multifunctional aziridine;

(c) a multifunctional aldehyde, and acetals and bisulfites thereof;

(d) a halohydrin;

(e) a multifunctional epoxy compound;

(f) a multifunctional carboxylic acid containing two to twelve carbon atoms, and methyl and ethyl esters, acid chlorides, and anhydrides derived therefrom;

(g) an organic titanate;

(h) a melamine resin;

(i) a hydroxymethyl urea; and (j) a multifunctional isocyanate.

24. The method of claim 3 wherein the surface crosslinking agent comprises ethylene glycol diglycidyl ether.

25. The method of claim 4 wherein the surface crosslinking agent comprises ethylene glycol diglycidyl ether.

26. The method of claim 3 wherein the wetted crosslinked poly(vinylamine) is heated at about 25° C. to about 150° C. for about 1 to about 15 minutes.

27. The method of claim 4 wherein the wetted crosslinked poly(vinylamine) is heated at about 25° C. to about 150° C. for about 1 to about 15 minutes.

* * * * *

UNITED STATES PATENT AND TRADEMARK OFFICE
CERTIFICATE OF CORRECTION

PATENT NO.: 5,981,689

DATED: November 9, 1999

INVENTOR: Mitchell *et al.*

It is certified that error appears in the above-identified patent and that said Letters Patent is hereby corrected as shown below:

Column 16, line 30, replace "react" with "reacts".

Column 16, line 46, replace "20%" with "--2%--".

Signed and Sealed this

Fifteenth Day of May, 2001

Attest:

NICHOLAS P. GODICI

Attesting Officer

Acting Director of the United States Patent and Trademark Office